United States Patent [19]

Eggensperger et al.

[11] Patent Number: 5,393,789
[45] Date of Patent: Feb. 28, 1995

[54] AMINE-AND ALCOHOL-BASED DISINFECTANT CONCENTRATE AND DISINFECTANT AND USE THEREOF

[75] Inventors: Heinz Eggensperger; Löwer Bernd, both of Hamburg; Michael Mohr, Kaltenkirchen; Peter Goroncy-Bermes, Ahrensburg; Wolfgang Beilfuss, Hamburg, all of Germany

[73] Assignee: Eastman Kodak Company, Rochester, N.Y.

[21] Appl. No.: 10,718

[22] Filed: Jan. 29, 1993

[30] Foreign Application Priority Data

Jan. 17, 1992 [DE] Germany .............................. 4201038

[51] Int. Cl.$^6$ ..................... A01N 33/04; A01N 31/14; C11D 9/50
[52] U.S. Cl. ................................... 514/674; 514/718; 252/106; 252/544; 252/153
[58] Field of Search ....................... 252/544, 153, 106; 514/674, 718

[56] References Cited

U.S. PATENT DOCUMENTS

| | | | |
|---|---|---|---|
| 3,592,918 | 7/1971 | Havers et al. | 514/674 |
| 4,853,411 | 8/1989 | Clarkson et al. | 514/441 |
| 5,185,145 | 2/1993 | Eggensperger et al. | 424/78.08 |
| 5,276,047 | 1/1994 | Eggensperger et al. | 514/674 |

FOREIGN PATENT DOCUMENTS

| | | |
|---|---|---|
| 0385369A2 | 2/1989 | European Pat. Off. . |
| 0333143A2 | 9/1989 | European Pat. Off. . |
| 0343605A1 | 11/1989 | European Pat. Off. . |
| 4005784A1 | 8/1991 | Germany . |

*Primary Examiner*—Paul Lieberman
*Assistant Examiner*—E. M. Higgins
*Attorney, Agent, or Firm*—John R. Everett

[57] ABSTRACT

The invention relates to a disinfectant concentrate which includes amine and alcohol and is characterized in that the alcohol component includes at least one aromatic alcohol and the amine component includes at least one tertiary alkyl amine which is free of hydroxyl groups. It is also relates to a disinfectant which is preparable from the disinfectant concentrate, and to the use of the disinfectant concentrate or disinfectant as a bactericide, in particular a Mycobactericide, fungicide or virucide.

2 Claims, No Drawings

AMINE-AND ALCOHOL-BASED DISINFECTANT CONCENTRATE AND DISINFECTANT AND USE THEREOF

FIELD OF THE INVENTION

The invention relates to an amine- and alcohol-based disinfectant concentrate, a disinfectant preparable therefrom and their use.

BACKGROUND

Disinfectants are used in many fields, serving to combat microorganisms. They are used for example for hand disinfection, operative field or wound disinfection, instrument disinfection, disinfection of surfaces, laundry etc. A matter of great interest is the effectiveness of disinfectants against Mycobacteria, in particular against tuberculosis exciters, which are relatively resistant, so that there is often no destruction, but merely a brief retardation of their increase. Over and above the bactericidal effectiveness, the fungicidal and virucidal effectiveness is also of interest. It is desirable that the action times of the disinfectants are as short as possible without thereby reducing the thoroughness and lastingness of the disinfection effect.

Known to date for example are disinfectants which contain one or more aldehydes or phenols as active ingredients.

Also known from EP 0 333 143 A2 is a liquid cleaning agent which contains a tertiary alkyl amine, in particular N,N-bis-(3-aminopropyl) lauryl amine as biocidal active ingredient, and also an anionic surfactant as necessary cleaning component. This cleaning agent can also contain water or alcohols with up to 4 carbon atoms such as methanol, ethanol etc. as solvents. It can be used as a disinfection cleaner, Further known from EP 0 343 605 A1 is a tuberculocidal disinfectant which includes N,N-bis-(3-aminopropyl)lauryl amine as disinfecting component. As well as a solvent mixture of water and an alcohol with up to 4 carbon atoms such as methanol, ethanol etc. it can also contain surfactants, quaternary ammonium compounds and complexing agents as cleaning agents.

Known from EP 0 385 369 A2 is a process for the antimicrobial preservation of liquid surfactants and surfactant-containing solutions, in which a preparation containing N,N-bis-(3-aminopropyl)lauryl amine is added to these liquids.

Further known from DE 40 05 784 A1 is a disinfectant concentrate which contains a cation-active compound and non-ionic surfactant as well as a phenoxy alcohol. The concentrate can contain amines or aminopolyols such as tetrakis-(2-hydroxypropyl)-N,N,N',N'-ethylene diamine as alkalization agents.

Disadvantages of the above-mentioned known disinfectants and disinfectant concentrates are that a) aldehyde- and phenol-containing disinfectants have a relatively strong and unpleasant odor, b) disinfectants based on amine and cation-active compounds or on aromatic alcohols and cation-active compounds shrink on surfaces (beads up) precisely because of the level of cation-active compounds and are incompatible with anionic surfactants, as they deactivate the latter. One disadvantage displayed by all preparations known to date is that relatively high concentrations of active ingredients are needed to achieve an adequate disinfection effect in a short period.

SUMMARY OF THE INVENTION

The object of the invention is therefore to provide a disinfectant or a concentrate of same whereby the disinfectant has both a substantially reduced active ingredient concentrations and an effectiveness equal to that of known disinfectants and, when it is applied, the action time needed to achieve the intended effect can be substantially reduced respectively. The disinfectant and the disinfectant concentrate are to be distinguished by a lack of odor and are also to be stable over an extended period and thus storable.

To achieve this object, a disinfectant concentrate or disinfectant is proposed which includes amine and alcohol and is characterized in that the alcohol component contains at least one aromatic alcohol and the amine component includes at least one tertiary alkyl amine free of hydroxyl groups.

Preferred versions of the disinfectant concentrate or disinfectant according to the invention are the subjects of the subsidiary claims.

The tertiary alkyl amine is an amine with the general formula:

$$R-N[(CH_2)_n-NH_2]_2,$$

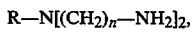

in which R is a $C_4$–$C_{20}$, in particular $C_6$–$C_{18}$ alkyl, $C_5$–$C_{10}$, in particular $C_6$ cycloalkyl, $C_7$–$C_{10}$, in particular $C_7$ aryl alkyl or $C_6$–$C_{14}$ in particular $C_6$ aryl group and n is a number from 2 to 10, preferably 2 to 6, particularly preferably 2 to 3.

R is preferably a $C_6$–$C_{18}$ alkyl group, more preferably a $C_{10}$–$C_{18}$ and particularly is preferably a dodecyl or tallow fat alkyl group. It is most preferred if R is a dodecyl group, i.e. the amine is N-(3-aminopropyl)-N-dodecyl-1,3-propanediamine or N,N-bis-(3-aminopropyl)lauryl amine, which can be obtained under the name "Lonzabac 12" from Lonza Ltd., Basle, Switzerland.

The aromatic alcohol is preferably a phenoxy alkanol, a phenyl monoglycol ether of an oligoglycol with up to 20 ethylene oxide units or a phenyl alkanol, in which the phenyl ring can be substituted in each case. $C_1$–$C_{18}$ alkyl groups in particular come into consideration as substituents. It is preferred if the aromatic alcohol is 2-phenoxy ethanol, 1-phenoxy-2-propanol, 2-phenoxy-1-propanol, 3-phenoxy-1-propanol, 1-phenoxy-2-butanol, 2-phenoxy-1-butanol, 1-phenyl ethyl alcohol, 2-phenyl ethyl alcohol, 3-phenyl-1-propanol, benzyl alcohol, a,4-dimethyl benzyl alcohol or a mixture of two or more of these compounds. Particularly preferred are phenoxy ethanol, phenoxy propanol and phenyl oligoglycol ether with 2 to 8, in particular 4 to 6 and especially 4 ethylene oxide units.

The aromatic alcohols according to the invention therefore also include mixtures of 1-phenoxy2-propanol and 2-phenoxy-1-propanol, e.g. in the ratio of 84:16, available under the trade name "Solvenon PP". The alcohol component can also be a mixture of 1-phenoxy-2-butanol and 2-phenoxy-1-butanol, e.g. in a mixture ratio of 94:6. Also suitable are phenyl oligoglycol ethers with preferably 4 ethylene oxide units (available under the trade name "Rewopal MPG 40"), which have the advantage vis-a-vis for example phenoxy ethanol or phenoxy propanol that they are miscible with water, are themselves effective in cleaning terms and are easy of access in economic terms.

As well as the above-mentioned constituents which are essential to the invention, the disinfectant concentrate or disinfectant can also contain normal additives such as solubilizers, corrosion protection agents, complexing agents, foam removers, stabilizers, buffers, perfume and/or dyestuffs.

Surprisingly, when the combination according to the invention of aromatic alcohol and tert.alkyl amine is used, the result is a synergistic biocidal effect which makes possible a reduction in the active ingredient content or a shortening of the action time.

The disinfectant concentrate generally contains 5 to 50 wt.-% of amine and 5 to 50 wt.-% of aromatic alcohol. In particular, it contains 10 to 20 wt.-% of tert.amine and 20 to 30 wt.-% of aromatic alcohol.

The ready-to-use disinfectant solution generally contains 0.1 to 10 wt.-% and preferably 1 to 5 wt.-% of the disinfectant concentrate and therefore generally 0.005 to 5 wt.-% of tert.amine and 0.005 to 5 wt.-% of aromatic alcohol. In particular, it contains 0.05 to 2.5 wt.-% of tert.amine and 0.05 to 2.5 wt.-% of aromatic alcohol, with 0.1 to 1.0 wt.-% of tert.amine and 0.2 to 1.5 wt.-% of aromatic alcohol being preferred.

When the disinfectant according to the invention is used, the desired disinfecting effect sets in already with action times of 15 minutes. If the use concentration of the concentrate in the working solution is increased, shorter action times are possible. The pH value of ready working solutions is generally in the range from 7 to 12, preferably 8 to 11 and particularly preferably 8.5 to 10.5.

The disinfectant concentrate or disinfectant preferably contains no cation-active compound. Because of the absence of cation-active compounds the danger does not arise that the disinfectant remains stuck, to a greater extent, to the substrate which is to be cleaned or shrinks on it and cannot be removed directly and completely by normal rinsing processes.

The active ingredient combination according to the invention can advantageously be combined with anionic and/or non-ionic surfactants, with anionic surfactants being preferred in respect of the cleaning effect and non-ionic surfactants or a combination of anionic and non-ionic surfactants in respect of the biocidal effect. Suitable anionic surfactants include alkyl sulphate, alkyl sulphonate, alkyl ether sulphate, alkyl aryl sulphonate, alkyl ether carboxylic acid or the alkaline or ammonium salt thereof, the alkyl group containing 8 to 18 carbon atoms, or a mixture of two or more of these compounds. Alkyl ether carboxylic acid with 2 to 10, in particular 3 to 5 ethylene oxide units is preferred.

Specially stable disinfectants and disinfectant concentrates result in particular from the addition of alkyl ether carboxylic acids, the disinfectant solutions displaying a high biocidal effectiveness and excellent cleaning activity.

The disinfectant or disinfectant concentrate according to the invention is a clear solution with very good stability which contains no precipitate even after prolonged storage, so that no losses of active ingredient occur through settling and use without previous fresh dissolution.

The disinfectants or disinfectant concentrates according to the invention display a good material compatibility with all conceivable substrates that will require cleaning.

The interface-active amine component also already produces a cleaning effectiveness which can be increased further by the additionally possible anionic or non-ionic surfactant content. Materials which have been treated can also be rinsed readily.

The biocidal effectiveness for example vis-a-vis *Aspergillus Niger, Pseudo-monas aeruginosa, Staphylococcus aureus, Proteus vulgaris* or *Candida albicans*, but in particular the effectiveness against Mycobacteria, is also found on surfaces and instruments.

The disinfectant concentrate and disinfectant according to the invention distinguish themselves in particular through lack of emissions, i.e. lack of odor, and a comparatively high flash point.

Compared with concentrates which contain merely the tertiary amine or the aromatic alcohol, the disinfectant concentrate according to the invention is distinguished by better technical applications properties, such as e.g. a lower viscosity and higher storage stability.

The main field of use of the disinfectant concentrate or disinfectant is the combatting of bacteria, in particular Mycobacteria, fungi and viruses.

The invention is explained in more detail below with the help of examples. In the examples the key to interpret the test results is as follows: Key: -= no growth
Furry Coating
(FC)>++++>+++>++>+>Several
(S)>Few(F)>Number
(Bacteria growth decreases in the order shown in the tables.)

EXAMPLES 1 to 9:

Microbiological effectiveness against Mycobact.terrae in instrument trial
Examples 1 to 3

Formulation

Example 1: 2 parts Lonzabac 12 in DM-H20

Example 2: 2 parts Lonzabac 12+2 parts phenoxy ethanol in DM-H20

Example 3: 2 parts phenoxy ethanol in DM-H20 (DM=demineralized water)

|  | Use Concentration | Action time | | | |
| --- | --- | --- | --- | --- | --- |
|  |  | 15 min | 30 min | 45 min | 60 min |
| Example 1: | conc. | S | — | — | — |
| Example 2: | conc. | — | — | — | — |
| Example 3: | conc. | ++++ | + | 3 | — |

Examples 4 to 6

Formulation

Example 4: 1.6 parts Lonzabac 12 in Dm-H20

Example 5: 1.6 parts Lonzabac 12+1.6 parts phenoxy ethanol in DM-H20

Example 6: 1.6 parts phenoxy ethanol in DM-H20

|  | Use Concentration | Action time | | | |
| --- | --- | --- | --- | --- | --- |
|  |  | 15 min | 30 min | 45 min | 60 min |
| Example 4: | conc. | 1 | — | — | — |
|  | 50% | + | — | — | — |
| Example 5: | conc. | — | — | — | — |
|  | 50% | F | — | — | — |
| Example 6: | conc. | ++++ | ++++ | +++ | ++ |
|  | 50% | ++++ | ++++ | ++++ | ++++ |

Result: In the instrument trial, the combination of Lonzabac 12 and phenoxy ethanol is more effective than the individual components against Mycobact.terrae.

Examples 7 to 9

Formulation

Example 7: 1.6 parts Lonzabac 12 in Dm-H20
Example 8: 2 parts Lonzabac 12+8 parts Rewopal MPG 40 in DM-H20 Example 9: 8 parts Rewopal MPG 40 in DM-H20

|  | Use Concentration (% Lonzabac 12) | Action time | | | |
|---|---|---|---|---|---|
|  |  | 15 min | 30 min | 45 min | 60 min |
| Example 7: | (1.6%) conc. | 1 | — | — | — |
|  | (0.8%) 50% | + | — | — | — |
|  | (0.4%) 25% | ++ | — | — | — |
| Example 8: | (2.0%) conc. | — | — | — | — |
|  | (1.0%) 50% | — | — | — | — |
|  | (0.5%) 25% | F | — | — | — |
|  | (0.25%) 12.5% | + | F | — | — |
| Example 9: | conc. | FC | FC | FC | FC |
|  | 50% | FC | FC | FC | FC |
|  | 25% | FC | FC | FC | FC |

Result: In the instrument trial, the combination of Lonzabac 12 and Rewopal MPG 40 is more effective than the individual components against Mycobact.terrae.

Examples 1 to 3 show that, with a 15-minute action time, the mixture (- = no growth) works better than the individual components (Lonzabac 12: S=several colony-forming units (CFUs), phenoxyethanol: strong growth).

Examples 4 to 6 show that a perceptible effect occurs with a 50% solution and a 15-minute action time, while there is a weaker effect with the concentrate. It also becomes clear that, with action times of up to 60 minutes, phenoxy ethanol makes no noteworthy contribution to the effect in either concentrated or dilute form. This makes the synergism clear.

EXAMPLES 10 to 12

The active ingredients were formulated with nonionic surfactants and isopropanol as auxiliaries at the concentration level of the disinfectant concentrates according to the invention (figures in wt.-%).

| Example | 10 | 11 | 12 |
|---|---|---|---|
| Lonzabac 12 | 10 | 10 | 10 |
| Phenoxy propanol | — | 20 | — |
| Phenoxy ethanol | — | — | 20 |
| C$_{10}$ oxo-alcohol with 11 EO (Lutensol ON 110) | 20 | 20 | 20 |
| Isopropanol | 10 | 10 | 10 |
| Water | 60 | 40 | 40 |

Effectiveness against Mycobacteria as per DGHM Guidelines (conc. and action time). DGHM refers to Deutsche Geseeschaft fur Hygiene und Mikrobiologie (German association for Hygiene and Microbiology).

| 1% | — | — | — |
|---|---|---|---|
| 2% | — | 60 min | 60 min |
| 3% | — | 45 min | 45 min |
| 5% | 60 min | 30 min | 30 min |

The increase in effect becomes clear particularly if phenoxy ethanol or phenoxy propanol is added to the amine (Lonzabac 12): the amine formulation works within half an hour in 5% concentration, the combination within an hour as 2% solution or within 30 minutes as 5% solution. In view of the ineffectiveness of phenoxy ethanol (see Examples 4 to 6), a synergism must be assumed which can be exploited by reducing the active ingredient: concentration or shortening the action time.

The following table with the formulations shows preferred versions of the disinfectant according to the invention in concentrate form, Formulation D being preferred in particular.

TABLE

| Constituents | A | B | C | D |
|---|---|---|---|---|
| Phenoxy ethanol | 30.0% | 30.0% | 30.0% | 30.0% |
| Lonzabac 12 | 12.0% | 12.0% | 12.0% | 12.0% |
| Isopropanol | 15.0% | 10.0% | 10.0% | 10.0% |
| Alkyl ethoxylate (11 EO) | 20.0% | — | — | — |
| Laureth-11-carboxylic acid* (Lauryl ether carboxylic acid with 11 EO) | — | 15.0% | 18.0 % | — |
| Laureth-5-carboxylic acid* (Lauryl ether carboxylic acid with 5 EO) | — | — | — | 18.0% |
| Water | — to 100% | | | |
| Blood purification 15 min: | almost residue-left | much residue left | some residue-free | almost residue-free |
| Storage at −5° C., appearance: | clear | clear | slightly clear | clouded |

*neutralized with soda lye

The invention has been described in detail with particular reference to preferred embodiments thereof, but it will be understood that variations and modifications can be effected within the spirit and scope of the invention.

We claim:

1. A ready for use disinfectant solution consisting essentially of from 0.005 to 5 wt. % of N,N-bis-(3-aminopropyl) lauryl amine and 0.005 to 5 wt. % of an aromatic alcohol selected from the group consisting of phenoxy ethanol, phenoxy propanol and a phenylmonoglycol ether oligoglycol having 4 ethylene oxide units.

2. The disinfectant composition according to claim 1 comprising 0.05 to 2.5 wt % of the amine and 0.05 to 2.5 wt % of the aromatic alcohol.

* * * * *